(12) United States Patent
Lee et al.

(10) Patent No.: US 6,455,693 B1
(45) Date of Patent: Sep. 24, 2002

(54) MOLECULAR RECTANGLES

(75) Inventors: Gene-Hsiang Lee; Shie-Ming Peng, both of Taipei; Chong-Mou Wang, Hsin-Tien; Kuang-Lieh Lu, Taipei, all of (TW); Balasubramanian Manimaran, Tamil Nadu (IN); Fang-Yuan Lee, Yunlin County (TW); Thangamuthu Rajandran, Tamil Nadu (IN)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/718,031

(22) Filed: Nov. 20, 2000

(51) Int. Cl.[7] .......................... C07F 11/00; C07F 13/00; C07F 15/00; C07F 15/02
(52) U.S. Cl. ..................... 540/145; 544/225; 544/226; 544/227; 546/2; 546/10
(58) Field of Search .................... 540/145; 544/225, 544/226, 227; 546/2, 10

(56) References Cited

PUBLICATIONS

Sujoy Baitalik et al., "Mononuclear and Binuclear Ruthenium (II) Complexes Containing 2,2'–Bipyridine or 1,10–Phenanthroline and Pyrazole–3,5–Bis(benzimidazole). Synthesis, Structure, Isomerism, Spectroscopy, and Proton–Coupled Redox Activity" Inorg. Chem., 38, 3296–3308 (1999).

Suzanne Belanger et al., "Thin–Film Molecular Materials Based on Terametallic "Squares": Nanoscale Porosity and Size–Selective Guest Transport Characteristics" J. Am. Chem. Soc., 121, 557–563 (1999).

Kurt D. Benkstein et al., "Molecular Rectangles Based on Rhenium(I) Coordination Chemistry" J. Am. Chem. Soc. 120, 12982–12983 (1998).

Kurt D. Benkstein et al., "Synthesis and Characterization of Molecular Rectangles Based upon Rhenium Thiolate Dimers" Inorg. Chem., 37, 5404–5405 (1998).

Dana L. Caulder et al., "The rational design of high symmetry coordination clusters" J. Chem. Soc., Dalton Trans., 1185–1200 (1999).

Jun Fan et al., "Self–Assembly of Porphyrin Arrays via Coordination to Transition Metal Biphosphine Complexes and the Unique Spectral Properties of the Product Metallacyclic Ensembles" J. Am. Chem. Soc., 121, 2741–2752 (1999).

Makoto Fujita et al., "Macrocyclic Polynuclear Complexes [(en)M(4,4'–bpy)]$_4$(NO$_3$)$_8$ (M=PD or Pt) as "Inorganic Cyclophane." Their Ability for Molecular Recognition" Tetrahedron Letters, vol. 32(40), 5589–5592 (1991).

(List continued on next page.)

Primary Examiner—Mukund J. Shah
Assistant Examiner—Thomas McKenzie
(74) Attorney, Agent, or Firm—Fish & Richardson P.C.

(57) ABSTRACT

The invention is based on the discovery that a new class of molecular rectangles can be prepared by using a stepwise synthesis plan under mild temperature conditions. The new rectangles are neutral and exhibit luminescence in solution at room temperature. In general, the invention features a compound having the structure:

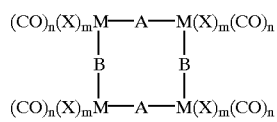

15 Claims, 2 Drawing Sheets

OTHER PUBLICATIONS

Makoto Fujita et al., "Supramolecular Self–Assembly of Macrocycles, Catenanes, and Cages through Coordination of Pyridine–Based Ligands to Transition Metals" Bull Chem. Soc. Jpn., 69, 1471–1482 (1996).

Paul J. Giordano et al., "The Nature of Lowest Excited State in fac–Tricarbonylhalobis (4–phenylpyridine)rhenium(I) and fac–Tricarbonylhalobis(4,4'–bipyridine)rhenium(I): Emissive Organometallic Complexes in Fluid Solution" Journal of American Chemical Society, 101(11) 2888–2897 (1979).

Frederick Guerin et al., "Synthesis and Reactivity of a New Intermediate Compound: $Na_4Sn$" J. Chem. Soc., Chem. Commun. 2213–2214 (1994).

Alistair J. Lees, "Luminescence Properties of Organometallic Complexes" Chem. Rev., 87, 711–743 (1987).

Bogdan Olenyuk et al., "Molecular architecture of cyclic nanostructures: use of co–ordination chemistry in the building of supermolecules with predefined geometric shapes" J. Chem. Soc., Dalton Trans., 1707–1728 (1998).

Thangamuthu Rajendran et al., "First Light–Emitting Neutral Molecular Rectangles" Abstract, The $8^{th}$ Asian Chemical Conference and Chemical Industry & Instrument Exhibition, Taipei, Taiwan, Nov. 21–24, 1999.

T. Rajendran et al., "First Light–Emitting Neutral Molecular Rectangles" Inorg. Chem. 39, 2016–2017 (2000).

T. Rajendran et al., "First–Light Emitting Neutral Molecular Rectangles" American Chemical Society Inorg. Chem., ic9912474 Supporting Info., 1–16 (2000).

Ram Sahai et al., "Complexes of Ruthenium (II) with $bpmRe(CO)_3Cl)_2$ as Ligands: Syntheses and Redox and Luminescence Properties" Inorg. Chem., 28, 1022–1028 (1989).

Robert V. Slone et al., "Luminescent Rhenium/Palladium Square Complex Exhibiting Excited State Intramolecular Electron Transfer Reactivity and Molecular Anion Sensing Characteristics" J. Am. Chem. Soc., 117, 11812–11814 (1995).

Robert V. Slone et al., "Self–Assembly of Luminescent Molecular Squares Featuring Octahedral Rhenium Corners" Inorg. Chem., 35, 4096–4097 (1996).

Robert V. Slone, et al., "Luminescent transition–metal–containing cyclophanes ("molecular squares"): covalent self–assembly, host–guest studies and preliminary nanoporous materials applications" Coordination Chemistry Reviews, 171, 221–243 (1998).

Peter J. Stang et al., "Mixed, Neutral–Charged, Platinum–Platinum and Platinum–Palladium Macrocyclic Tetranuclear Complexes" Organometallics, 13, 3776–3777, (1994).

Peter J. Stang et al., "Self–Assembly of Cationic, Tetranuclear, (Pt(II) and Pd(II) Macrocyclic Squares. X–ray Crystal Structure of $[Pt^2+(dppp)(4,4'-bipyridyl)2^- OSO_2CF_3]_4$," J. Am. Chem. Soc., 117, 6273–6283 (1995).

Peter J. Stang et al., "Directed Self–Assembly of Chiral, Optically Active Macrocyclic Tetranuclear Molecular Squares" Angew. Chem. Int. Ed. Engl., 35(7), 732–736 (1996).

Peter J. Stang et al., "Molecular architecture via coordination: self–assembly of cyclic cationic porphyrin aggregates via transition–metal bisphosphane auxiliaries" Chem. Commun., 1453–1454 (1997).

Peter J.Stang et al., "Self–Assembly, Symmetry, and Molecular Architecture: Coordination as the Motif in the Rational Design of Supramolecular Metallacyclic Polygons and Polyhedra" Acc. Chem. Res., 30, 502–518 (1997).

Shih–Sheng Sun et al., "New Self–Assembly Luminescent Molecular Triangle and Square Rhenium(I) Complexes" Inorg. Chem., 38, 4181–4182 (1999).

Stephen M. Woessner et al., "Self–Assembly of Ligand–Bridged Molecular Rectangles Containing $fac-Re(CO)_3$ Corners" Inorg. Chem., 37, 5406–5407 (1998).

Karl Ziemelis, "Glowing developments" Nature, 399, 408–409 (Jun. 3, 1999).

MOLECULAR RECTANGLES

FIELD OF THE INVENTION

This invention relates to transition metal complexes, and more particularly to neutral, luminescent complexes having rectangular structures.

BACKGROUND OF THE INVENTION

The desirability of neutral molecular rectangles for molecular recognition and separation applications has been previously reported (Belanger et al., *J. Am. Chem. Soc.*, 121:557–563, 1999).

Supramolecular structures containing transition metal ions with potential inclusion and host-guest applications have been extensively explored in recent years (Stang et al., *J. Chem. Commun.*, 1453–1454, 1997; Stang et al., *J. Am. Chem. Soc.*, 117:6273–6283, 1995; Stang et al., *Organometallics*, 13:3776–3777, 1994; Caulder et al., *J. Chem. Soc., Dalton Trans.*, 1185–1200, 1999; Fujita et al., *Bull. Chem. Soc. Jpn.*, 69:1471–1482, 1996; Fujita et al., *Tetrahedron Lett.*, 32:5589–5592, 1991; Lehn et al., *Supramolecular Chemistry: Concepts and Perspectives*, VCH: Weinheim, 1995; Drain et al., *J. Chem. Soc., Chem. Commun.*, 2313–2315, 1994). Stang and co-workers contributed to the formation of a combinatorial library of cyclic molecular polygons via the systematic combination of building blocks with predetermined angles (Olenyuk et al., *J. Chem. Soc., Dalton Trans.*, 1707–1728, 1998).

The initial focus was directed toward molecular squares, i.e., macrocycles fabricated by cis-coordinated transition metal corners and rigid or semirigid bifunctional ligand edges (Fan et al., *J. Am. Chem. Soc.*, 121:2741–2752, 1999; Stang et al., *Angew. Chem., Int. Ed. Engl.*, 35:732–736, 1996; Stang et al., *Acc. Chem. Res.*, 30:502–518, 1997; Belanger et al., supra; Slone et al., *Coord. Chem. Rev.*, 171:221–243, 1998; Slone et al., *J. Am. Chem. Soc.*, 117:11813–11814, 1995; Sun et al., *Inorg. Chem.*, 38:4181–4182, 1999).

Subsequent efforts were devoted to the synthesis of molecular rectangles to improve selectivity and sensitivity in molecular recognition and separation (Benkstein et al., *Inorg. Chem.*, 37:5404–5405, 1998; Benkstein et al., *J. Am. Chem. Soc.*, 120:12982–12983, 1998; Slone et al., *Inorg. Chem.*, 35:4096–4097, 1996; Woessner et al., *Inorg. Chem.*, 37:5406–5407, 1998). Hupp et al. were the first to report the preparation of rhenium thiolate-based rectangles that exhibited interesting electrochemistry. Subsequent work by the same group led to the synthesis, characterization, and preliminary binding properties of a new class of tetracationic rectangular molecules with triflate as counterion (Benkstein et al., supra). To tune the cavity size, Sullivan et al. recently also reported the preparation of a series of molecular rectangles based on fac-Re-(CO)$_3$ corners containing 4,4'-bipyridine as one side and two $\eta^2$-alkoxy or hydroxy bridges as the other (Woessner et al., supra).

All molecular rectangles reported thus far have had a net charge, however, and thus required counterions within their channels. Past attempts to make neutral rectangles have exclusively yielded molecular squares (Benkstein et al., supra).

Accordingly, a need exists for a method of preparing neutral molecular rectangles.

SUMMARY OF THE INVENTION

The invention is based on the discovery that a new class of molecular rectangles can be prepared by using a stepwise synthesis plan under mild temperature conditions. The new rectangles are neutral and exhibit luminescence in solution at room temperature.

In general, the invention features a compound having the structure:

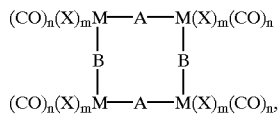

where M is a transition metal; A and B, indepedently, are neutral bidentate ligands; n is 1, 2, 3, or 4; m is 0, 1, or 2; and X is chlorine (Cl), bromine (Br), or iodine (I).

M can be, for example, iron (Fe), ruthenium (Ru), or osmium (Os), in which cases, n and m can each be 2; rhenium (Re) or manganese (Mn), in which cases n can be 3, and m can be 1; or chromium (Cr), molybdenum (Mo), or tungsten (W), in which cases n can be 4, and m can be 0.

A and B can be, independently, unsubstituted or substituted 4,4'-polypridyl ligands, or can be selected from the group consisting of:

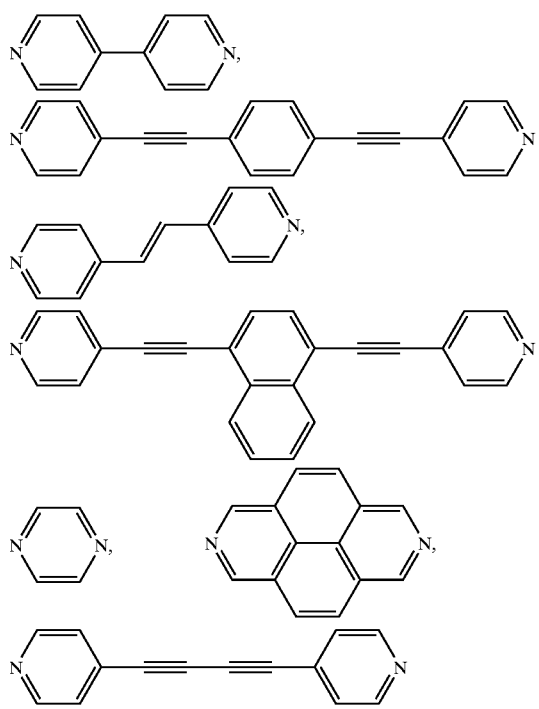

-continued

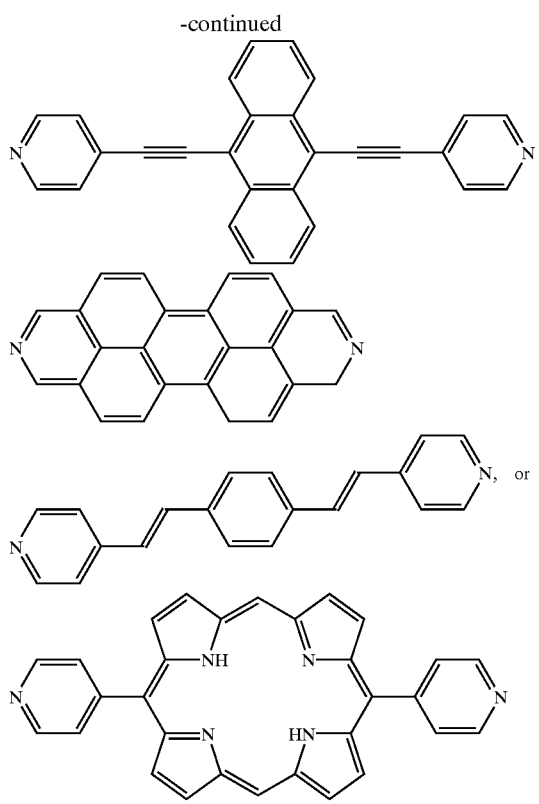

and substituted derivatives thereof.

In some cases, X is Br, A is

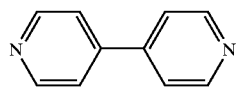

and B is

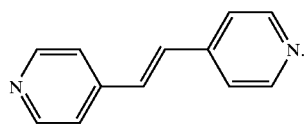

In other cases, X is Br, A is

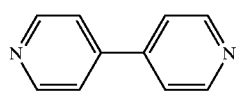

and B is

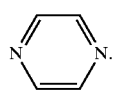

In still other cases, X is Br, A is

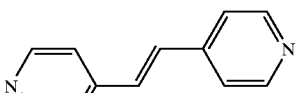

and B is

The invention also features a method of making a compound having the structure:

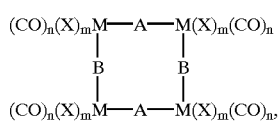

where M is a transition metal; A and B, indepedently, are neutral bidentate ligands;

n is 1, 2, 3, or 4; m is 0, 1, or 2; and X is Cl, Br, or I. The method features the steps of: (a) reacting $M(X)_m(CO)_{n+2}$ with trimethylamine N-oxide in the presence of acetonitrile to form: $M(X)_m(CO)_{n+1}(NCCH_3)$; (b) reacting $M(X)_m(CO)_{n+1}(NCCH_3)$ with bidentate ligand A to form: $(CO)_{n+1}(X)_mM$—A—$M(X)_m(CO)_{n+1}$; (c) reacting $(CO)_{n+1}(X)_mM$—A—$M(X)_m(CO)_{n+1}$ with trimethylamine N-oxide in the presence of acetonitrile to form: $(CH_3CN)(CO)_n(X)_mM$—A—$M(X)_m(CO)_n(NCCH_3)$; and (d) reacting $(CH_3CN)(CO)_n(X)_mM$—A—$M(X)_n(CO)_n(NCCH_3)$ with bidentate ligand B to form the compound having the structure:

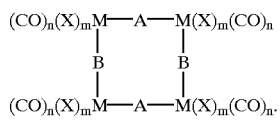

The invention also features a method for forming a thin film on a substrate. The method includes the steps of: (a) preparing a solution of a molecule rectangle of claim 1; (b) dip coating or spraying the substrate with the solution; and (c) drying the substrate to form a thin film of the molecular rectangle on the surface of the substrate. The substrate can be, for example, an electrode such as a gold or glassy carbon electrode.

The invention also features a method for differentiating redox substances of different sizes. The method includes the steps of: (a) coating an electrode with a molecular rectangle of claim 1; and (b) measuring the redox potential of a solution to differentiate redox substances present in the solution.

The invention also features a method for separating metal coordination complexes. The method includes the steps of: (a) coating an electrode with a molecular rectangle of claim 1; and (b) passing a solution containing metal coordination complexes through the coated electrode while applying a potential, to separate the coordination complexes.

The invention also features a method for photodegradation of chemicals. The method includes the steps of: (a)

treating the chemicals with a solution comprising vitamin $B_{12}$ and a molecular rectangle of claim 1; and (b) photoactivating the molecular rectangle by UV irradiation to form an active species that reduces vitamin $B_{12}$ to a species that degrades the chemicals. The chemicals can include, for example, one or more haloalkanes.

As used herein, the terms "rectangle" and "molecular rectangle" refer to transition metal complexes having four metal atoms M connected in a rectangular geometry via two pairs of bridging ligands (i.e., 2 A and 2 B). Optionally, additional ligands L can be attached to the metal atoms. Such rectangles are generally depicted by the formula:

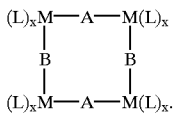

The invention provides several advantages. For example, the new molecular rectangles exhibit luminescence in solution at room temperature. Since the luminescence of these molecules is sensitive to the environment, the new rectangles can be used as luminescent sensors. Changes in the environment of the molecules can be detected by monitoring changes in luminescence intensity or lifetime.

Host-guest chemistry is an important area of study in the field of supramolecular chemistry. Many of the previously reported rectangles have been charged and have had small cavities. Counterions can become trapped inside the cavity of charged rectangles, and can thereby interfere with host-guest chemistry or affect molecular sensing properties. In contrast, the new molecular rectangles are neutral and have no counterions inside their channels. The new molecular rectangles also possess large cavities, making them suitable as hosts for many molecules of varying sizes, or for use in inclusion studies.

Molecular rectangles can exhibit greater selectivity with respect to molecular size than can squares, allowing them to find use in molecular sieves.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
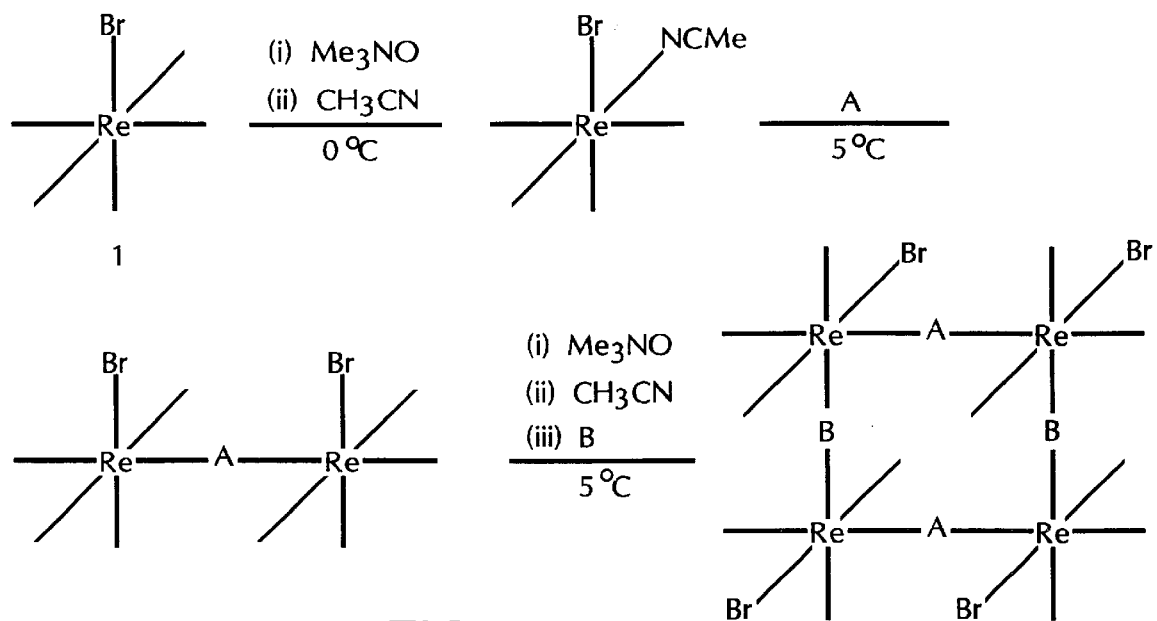
FIG. 1 is a synthetic scheme for preparing molecular rectangles of the invention.

The invention provides new molecular rectangles and methods of synthesizing and using the new rectangles.

Synthesis of Molecular Rectangles

In general, the molecular rectangles can be prepared in a two-stage method. The first stage is the preparation of a bimetallic edge, and the second stage is the coupling of two bimetallic edges to form the molecular rectangle.

In the first stage, a metal complex such as $M(X)_m(CO)_{n+2}$ (e.g., where M is Re, Fe, Os, Ru, Co, Rh, Ir, Cr, Mo, W) is activated with, for example, trimethylamine N-oxide, or via thermolysis. The activated complex can then be reacted with a first bidentate ligand such as a 4,4'-polypyridyl ligand to form bimetallic edges.

In the second stage, the two metal centers of the bimetallic edges are activated again (i.e., chemically or thermally, as described above). The activated edges can then be reacted with a second bidentate ligand to form the molecular rectangles.

The reactions can be carried out under a wide range of conditions. For example, reaction of the metal complexes and bimetallic edges with the bidentate ligands can proceed at between about 0° C. and about 100° C. in acetonitrile or other solvent, and can take from about 1 hour to about 6 hours (e.g., about 4 hours).

Uses of Molecular Rectangles

The molecular rectangles of the invention can form thin films on many types of electrodes, including gold, glassy carbon, and ITO conductive glass electrodes, or on other substrates. For example, a desired molecular rectangle can be dissolved in chloroform to a concentration of 0.1 mM. The resulting solution can be used for dip coating a substrate surface. The coating can then be air-dried (e.g., at ambient temperature). A quantity of the rectangle (e.g., about 30 $\mu$l/cm$^2$) is thus deposited on the surface.

The rectangles also exhibit the ability to differentiate redox substrates of different sizes. Experiments have shown that redox molecules such as $[Fe(CN)_6]^{3-}$, $[Ru(NH_3)_6]^{3+}$, and [methylviologen]$^{2+}$ can be differentiated by making use of the molecular rectangles' size exclusion properties. Without wishing to be bound by any theory, it is believed that large redox molecules have more difficulty in approaching double layer molecular rectangle-modified electrodes than do smaller redox molecules, and that the electron exchange between the redox couple and electrode is accordingly slower for the larger redox molecules.

The rectangles can also be used in applications such as ultrafiltration, molecular separation, and optical rectification. Since the new molecular rectangles can have cavities of different dimensions, they can allow only permeants of appropriate sizes to pass. For example, if molecules like ferrocene methanol, $[Ru(NH_3)_6]^{3+}$, $[Fe(CN)_6]^{3-}$, $[Ru(NH_3)_5(py)]^{2+}$, $[Ru(NH_3)_5(4\text{-pic})]^{2+}$, $[Fe(2,2'\text{-bpy})_3]^{2+}$, $[Co(2,2'\text{-bpy})_3]^{2+}$, $[Fe(bphenSO_3)_3]^{4-}$ were allowed to pass through a film made up of the new molecular rectangles (e.g., coated on an electrode), some selectivity in the molecular separation could be expected (e.g., based on size) when a potential was applied.

Because the molecular rectangles can act as reducing agents upon excitation, they can be used in the photodegradation of harmful chemicals such as dibromoalkanes with the incorporation of vitamin $B_{12}$. The reaction can be depicted as follows:

Rectangle+hv→[Rectangle]*

[Rectangle]*+$B_{12}$→[Rectangle]⁺+B12⁻

$2B_{12}^-$+dibromomethane→$2B_{12}$+alkene +2 Br⁻

The reaction can be, for example, carried out in a medium such as 1% Triton X-100 aqueous emulsion. It is possible that solid-state reactions can alternatively be used.

Light-emitting rectangles can also be used as sensors in host-guest chemistry and in molecular recognition. Thus, for example, they can be used in place of existing sensors such as Ru(II) polypyridyl complexes and many Re-based compounds. The molecular rectangles can be useful for chemical sensing applications (e.g., for the detection of oxygen). The new molecular rectangles may offer advantages over existing sensors.

The invention will be further described in the following examples, which do not limit the scope of the invention described in the claims.

EXAMPLES

Example 1
Synthesis of Molecular Rectangles

Referring to FIG. 1, activation of Re(CO)₅Br 1 with trimethylamine N-oxide (Me₃NO) at 0° C. followed by addition of 0.5 equivalents of 4,4'-bipyridine (bpy) in toluene gave a pale-yellow, shiny edge product [Re(CO)₄Br]₂(μ-bpy) 2a in 58% yield. Further treatment of edge 2a at 5° C. in methylene chloride with 2 equivalents of trimethylamine N-oxide oxide and acetonitrile yielded intermediate [(Re(CO)₃(NCMe)Br]₂(μ-bpy), which was then titrated with pyrazine (pyr) to produce molecular rectangle 3a in 24% yield.

By substituting trans-1,2-bis-(4-pyridyl)ethylene (bpe) for pyr, molecular rectangle 3b was prepared in 13% yield by the same method as was used for molecular rectangle 3a. Similarly, by substituting pyr for bpy, and bpe for pyr, molecular rectangle 3c was also prepared in 14% yield by the same method.

Rectangles 3a, 3b, and 3c and their corresponding edges 2a, 2b, and 2c were characterized spectroscopically. FAB-MS analyses of 3a and 2a exhibited signals corresponding to the molecular ions at m/z -1880 and m/z=916, respectively, with the experimental isotope pattern matching the calculated values. The ¹H-NMR spectrum of 3a indicated the presence of two predominant isomeric forms in solution at room temperature, most likely due to the orientation of the CO/Br trans-ligand pairs with respect to the plane containing the Re atoms.

Example 2
Analysis of Molecular Rectangles

Figure 2:
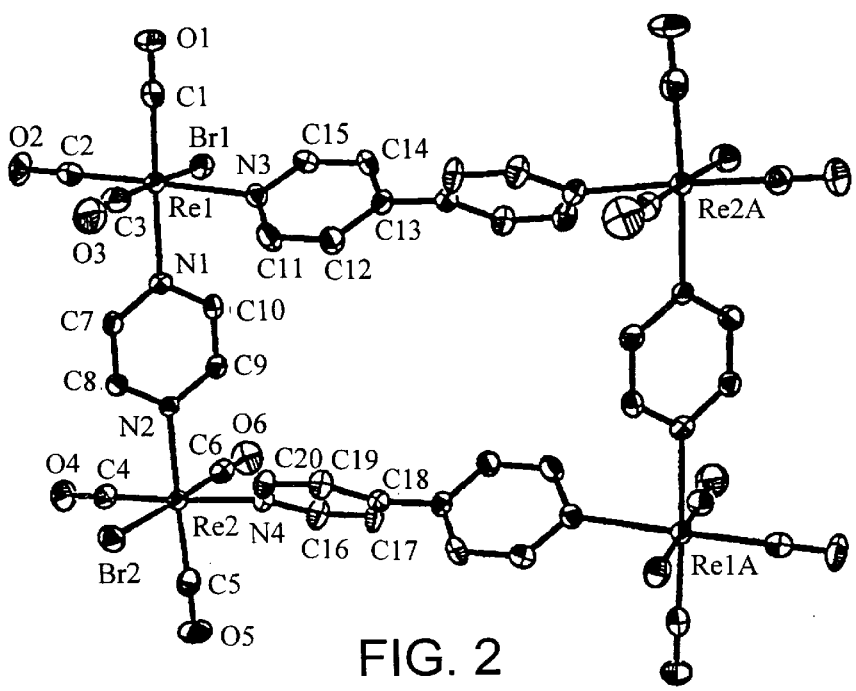
FIG. 2 is an ORTEP diagram of a molecular rectangle of the invention.

Yellow, monoclinic crystals of 3a (space group P21/c, a=12.0890(2) Å, b=24.2982(2) Å, c=12.8721(2) Å, β=107.923(1)°, V=3597.57(9) Å³, ρ=2.051 Mg/m³, Z=2, T=150 K; of 18,370 reflections (2θ<52°) measured, 7,285 with I>2σ(I) were used to refine 451 parameters; R=0.0356 and wR(F²)=0.0693) were grown from acetone, and X-ray diffraction studies were carried out. An ORTEP diagram of 3a is shown in FIG. 2. The structure includes a molecular rectangle in which two Br(CO)₄Re-bpy-Re(CO)₄Br edges are bridged by two pyrazine (pyr) moieties. In each bipyridine (bpy) moiety, one of the aromatic rings was found to have a canted configuration with respect to the plane of the other rings. The Br(1) and Br(2) were disordered with the CO group in 73/27 occupancy, which was substantiated by the isomeric ¹H-NMR spectral pattern of 3a. Average bond distances were as follows: Re-C(CO), 1.92 Å; Re-N(4,4'-bpy), 2.22 Å; Re-N(pz), 2.21 Å. These distances are similar to those observed for a number of other Re(I) complexes (Belanger et al., supra; Woessner et al., supra). The molecular rectangle 3a was found to have a cavity with dimensions 11.44 Å×7.21 Å. Since no steric hindrance should exist between the Re metal centers, the cavity size can be fine-tuned. For example, in molecular rectangle 3b, a cavity with dimensions of 11.38 Å×13.17 Å is expected from molecular modeling studies. The packing diagram of molecular rectangle 3a shows the effective π stacking of the aromatic rings that ensures the close packing of the molecules to form an infinite number of open-end channels.

IR spectroscopy showed that the CO stretching frequency ($v_{CO}$) shifted bathochromatically from 2113 to 2032 cm⁻¹ when edge 2a was converted into molecular rectangle 3a. This red shift in $v_{CO}$ indicates that new linkages were formed between the additional π ligands and the metal center. In addition, edge compounds 2a, 2b, and 2c, and molecular rectangles 3a, 3b, and 3c each exhibited two absorption bands in the near-UV region of the spectrum. Without being bound by theory, it is likely that the absorption band at higher energy (i.e., 251–265 nm) is attributable to a π–π* transition, and that the band at lower energy (i.e., 315–342 nm) is attributable to metal-to-ligand charge transfer (MLCT). Control experiments indicated that the MLCT bands were insensitive to the variation of the halide, whereas a substitution of CO with other ligands shifted the MLCT band bathochromatically. Examination of the UV-vis absorption spectra showed that the MLCT maximum of edge 2a is centered at 315 NM, whereas for molecular rectangle 3a it is at 324 nm. This spectral difference suggests that the ground state of edge 2a is raised to a higher level in the conversion to molecular rectangle 3a.

Example 3
Fluorescence Properties of Molecular Rectangles

Edges 2a, 2b, and 2c, and molecular rectangles 3a, 3b, and 3c, all fluoresced with quantum yields of about 0.002 relative to Ru(bpy)₃²⁺. The electronic absorption maxima, excited-state emission maxima, emission lifetimes, and emission quantum yields are indicated in Table 1:

TABLE 1

| Complex | λ_max (nm)[a] Ligand | λ_max (nm)[a] MLCT | λ_max (nm)[a] Emission | τ (ns)[a] | Φ_cm[b] |
|---|---|---|---|---|---|
| 2a | 263 | 315 | 412,563 | 228 | 0.0017 |
| 2b | 265 | 320 | 452 | 16 | 0.0031 |
| 2c | 262 | 322 | 541 | 17 | 0.0014 |
| 3a | 254 | 324 | 416,563 | 14 | 0.0010 |
| 3b | 252 | 329 | 467 | 11 | 0.0014 |
| 3c | 251 | 342 | 385,470,558 | 15 | 0.0022 |

[a]Measured in deoxygenated acetonitrile at 298K.
[b]Emission quantum yield measured at 298K. $\lambda_{ex}$ = 436 nm with reference to [Ru(bpy)$_3$]$^{2+}$ ($\Phi_{cm}$ = 0.0420); error is ± 10%.

Cyclic voltammetry (CV) spectra revealed that electron exchange through an electrode such as glassy carbon occurred near the potential of E≧1.0 V vs. SCE. Therefore, edge compounds 2a, 2b, and 2c, and molecular rectangles 3a, 3b, and 3c, can be expected to be strong reducing agents upon photoexcitation. Combining the energy gap between the ground state and the MLCT excited state as well as the formal potentials of the molecular rectangles 3a, 3b, and 3c (+/0), formal potentials at the excited state were estimated to be about −1 V vs. SCE. Thus, molecular rectangles 3a, 3b, and 3c can reduce methyl viologen (MV$^{2+}$, $E^{0'}_1$≈−0.4 V; $E^{0'}_2$≈−0.7 V vs. SCE) or tetracyanoquinodimethane (TCNQ, $E^{0'}_1$≈−0.3 V vs. SCE). Preliminary results with molecular rectangle 3a are in full accord with this hypothesis. The excited state of rectangle 3a can be oxidatively quenched by TCNQ; the Stern-Volmer quenching rate constant is estimated to be $10^5$ M$^{-1}$ s$^{-1}$ at 25° C.

Example 4

Differentiation of Redox Substrates using Molecular Rectangles

Figure 3:
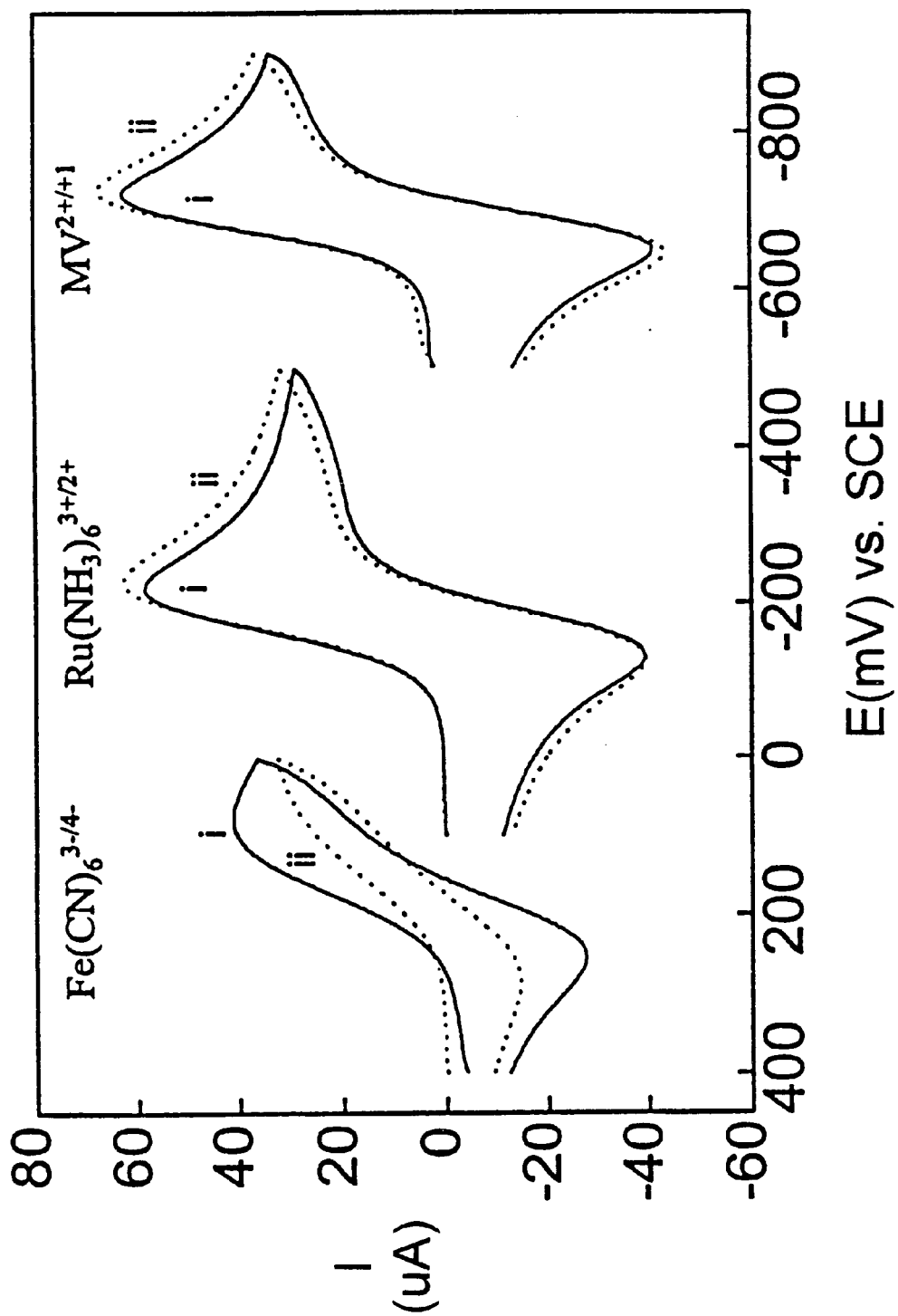
FIG. 3 is a plot of cathodic current ($\mu$A) vs. voltage (mV relative to a standard calomel electrode, "SCE") for three redox couples using bare electrodes (solid lines) and electrodes coated with molecular rectangles of the invention (dotted lines).

Molecular rectangle 3a was dissolved in chloroform to a concentration of 0.1 mM. A portion of the solution (i.e., about 30 μl/cm$^2$) was then dip coated on the surface of an ITO conductive glass electrode. Studies with Fe(CN)$_6^{3−/4−}$ (d~6 Å), Ru(NH$_3$)$_6^{3+/2+}$ (d~5.5 Å) and methyl viologen (denoted MV$^{2+/+/0}$) with the modified electrode revealed that the Fe(CN)$_6^{3−/4−}$ redox couple was blocked by the rectangle film. As shown in FIG. 3, the electroactivity reflected in the cathodic current was noticeably less significant for the bulkier ruthenium and MV redox couples. In FIG. 3, the solid line traces were recorded with a bare electrode, and the dotted line traces were measured with the modified electrode in potassium nitrate solution.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A molecular rectangle compound having the structure:

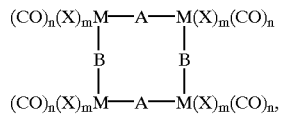

wherein

M is a transition metal selected from the group consisting of iron, ruthenium, osmium, rhenium, manganese, chromuim, molybdenum, and tungsten;

A and B are non-identical and, independently, are selected from the group consisting of

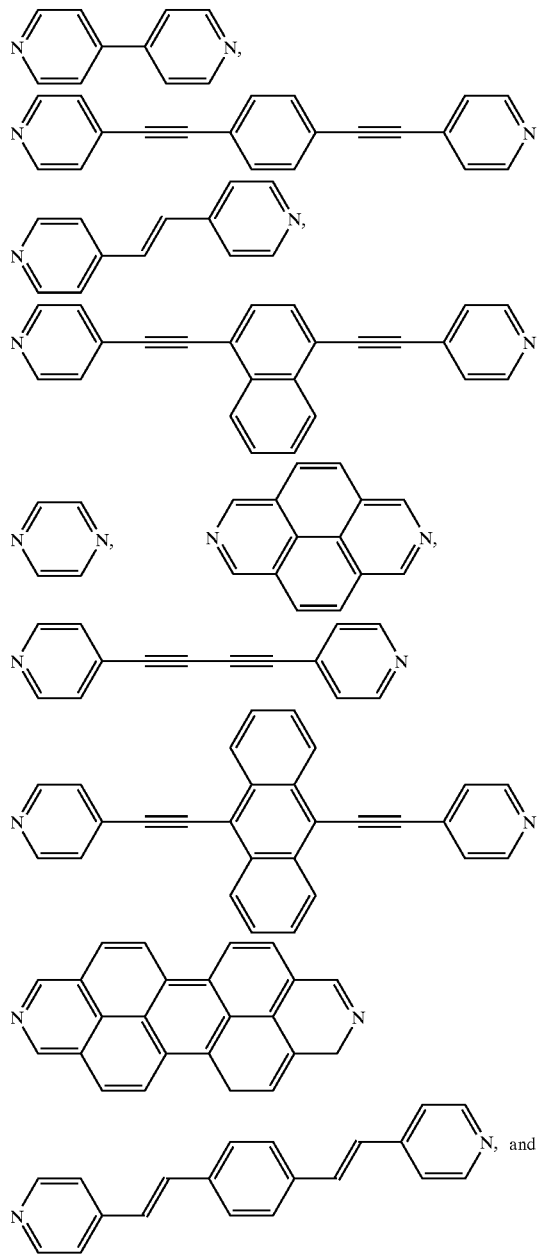

-continued

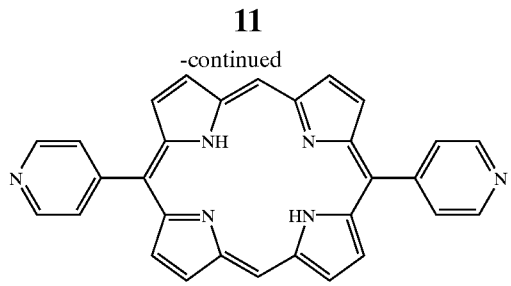

and substituted derivatives thereof;

n is 1, 2, 3, or 4;

m is 0, 1, or 2; and

X is chlorine (Cl), bromine (Br), or iodine (I).

2. The compound of claim 1, wherein M is iron (Fe), n is 2, and m is 2.

3. The compound of claim 1, wherein M is ruthenium (Ru), n is 2, and m is 2.

4. The compound of claim 1, wherein M is osmium (Os), n is 2, and m is 2.

5. The compound of claim 1, wherein M is rhenium (Re), n is 3, and m is 1.

6. The compound of claim 1, wherein M is manganese (Mn), n is 3, and m is 1.

7. The compound of claim 1, wherein M is chromium (Cr), n is 4, and m is 0.

8. The compound of claim 1, wherein M is molybdenum (Mo), n is 4, and m is 0.

9. The compound of claim 1, wherein M is tungsten (W), n is 4, and m is 0.

10. The compound of claim 5 wherein X is Br, A is

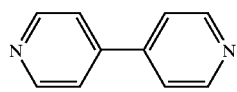

and B is

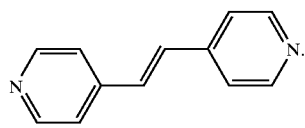

11. The compound of claim 5, wherein X is Br, A is

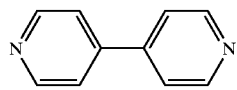

and B is

12. The compound of claim 5, wherein X is Br, A is

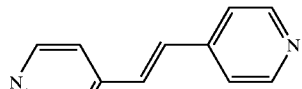

and B is

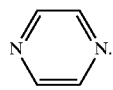

13. A method for forming a thin film on an electrode, the method comprising:

(a) preparing a solution of a molecule rectangle compound of claim 1;

(b) dip coating or spraying the electrode with the solution; and (c) drying the electrode to form a thin film of the molecular rectangle compound on the surface of the substrate.

14. The method of claim 13, wherein the electrode comprises gold or glassy carbon.

15. A method of making a molecular rectangle compound having the structure:

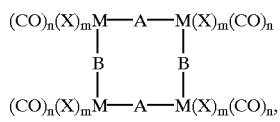

wherein

M is a transition metal selected from the group consisting of iron, ruthenium, osmium, rhenium, manganese, chromuim, molybdenum, and tungsten;

A and B are non-identical and, indepedently, are selected from the group consisting of

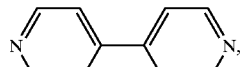

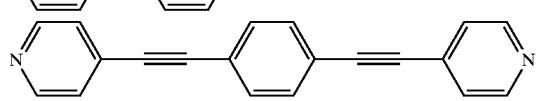

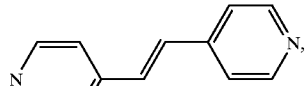

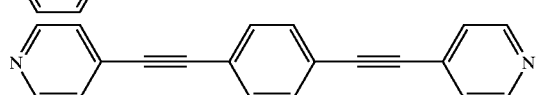

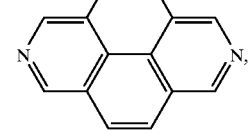

-continued

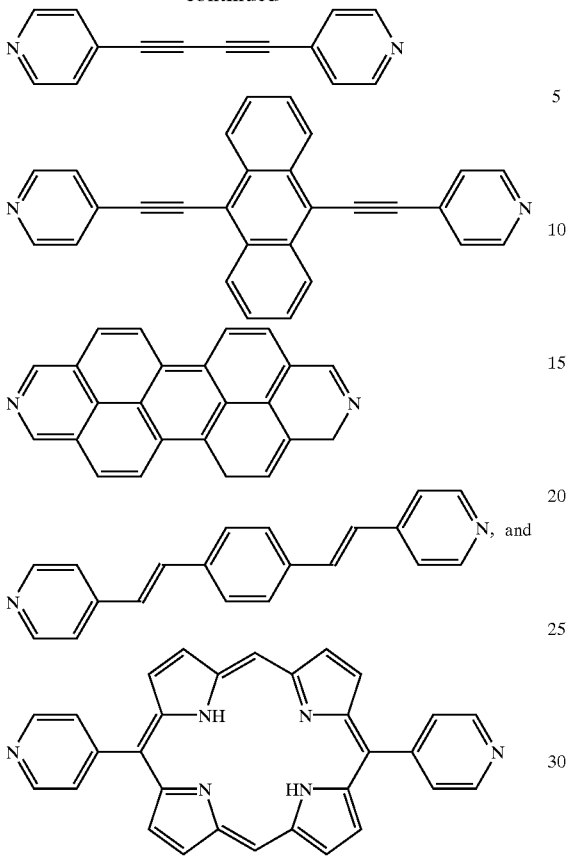

and substituted derivatives thereof;
n is 1, 2, 3, or 4;
m is 0, 1, or 2; and
X is Cl, Br, or I;
the method comprising:

(a) reacting $M(X)_m(CO)_{n+2}$ with trimethylamine N-oxide in the presence of acetonitrile to form:

$M(X)_m(CO)_{n+1}(NCCH_3)$;

(b) reacting $M(X)_m(CO)_{n+1}(NCCH_3)$ with bidentate ligand A to form:

$(CO)_{n+1}(X)_mM\text{—}A\text{—}M(X)_m(CO)_{n+1}$;

(c) reacting $(CO)_{n+1}(X)_mM\text{—}A\text{—}M(X)_m(CO)_{n+1}$ with trimethylamine N-oxide in the presence of acetonitrile to form:

$(CH_3CN)(CO)_n(X)_mM\text{—}A\text{—}M(X)_m(CO)_n(NCCH_3)$;

and (d) reacting $(CH_3CN)(CO)_n(X)_mM\text{—}A\text{—}M(X)_m(CO)_n(NCCH_3)$ with bidentate ligand B to form the molecular rectangle compound having the structure:

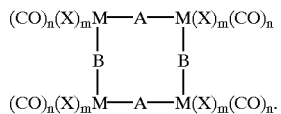

* * * * *